US012653998B2

(12) United States Patent
Kumar et al.

(10) Patent No.: US 12,653,998 B2
(45) Date of Patent: Jun. 16, 2026

(54) DISINFECTING CAP FOR MALE AND FEMALE CONNECTORS INCLUDING A CONSTRICTING LOCK

(71) Applicant: Becton, Dickinson and Company, Franklin Lakes, NJ (US)

(72) Inventors: Manish Kumar, Bengaluru (IN); Praveen Nalawade, Belagavi (IN); Shashwat Jain, Indore (IN); Kadamb Gupta, Greater Noida (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 712 days.

(21) Appl. No.: 17/994,929

(22) Filed: Nov. 28, 2022

(65) Prior Publication Data

US 2024/0173531 A1     May 30, 2024

(51) Int. Cl.
*A61M 39/16*     (2006.01)
*A61M 39/10*     (2006.01)
*A61M 39/20*     (2006.01)

(52) U.S. Cl.
CPC ...... *A61M 39/162* (2013.01); *A61M 39/1011* (2013.01); *A61M 39/165* (2013.01); *A61M 39/20* (2013.01)

(58) Field of Classification Search
CPC .. A61M 39/162; A61M 39/165; A61M 39/16; A61M 39/10; A61M 39/20; A61M 39/1011; A61M 39/00; A61M 39/1055; A61M 2005/3104; A61M 2005/3106; A61M 2005/312; A61M 5/3202; A61M 5/3216; A61M 5/5086; A61M 5/001; A61M 2039/0288; A61M 2039/1066;

A61M 2039/1077; A61M 2039/1083; A61M 2039/1088; A61M 2039/1033; A61M 2039/1038; A61M 2205/0205;
(Continued)

(56) References Cited

U.S. PATENT DOCUMENTS 8,197,749 B2    6/2012  Howlett et al.
8,671,496 B2    3/2014  Vaillancourt et al.
(Continued)

FOREIGN PATENT DOCUMENTS

WO       2022006264 A1    1/2022

*Primary Examiner* — Brandy S Lee
*Assistant Examiner* — Alexandra Lalonde
(74) *Attorney, Agent, or Firm* — Servilla Whitney LLC

(57)     ABSTRACT

A cap configured to engage connectors of different types includes a housing having an open first end, a second end, a sidewall extending between the first end and the second end, and an opening extending through the sidewall. The cap further includes a flexible sleeve disposed in the housing having a first end, a second end, and a sleeve sidewall extending between the first end of the flexible sleeve and the second end of the flexible sleeve. The cap further includes: a lock connected to the housing configured to move through the opening extending through the sidewall of the housing to press against the sleeve sidewall, which causes the sleeve sidewall to directly or indirectly press against a portion of a connector of the connectors to secure the connector in the housing; and an absorbent member disposed in the flexible sleeve configured to contain a cleaning solution for cleaning and/or disinfecting portions of the connector engaged to the cap.

20 Claims, 11 Drawing Sheets

(58) Field of Classification Search
CPC .... A61M 2205/273; A61M 2025/0019; A61M 2025/0056; Y10S 604/905; A61J 1/1412; A61J 1/18; F16L 55/115; B08B 1/14; A61B 90/70
See application file for complete search history.

(56) References Cited

U.S. PATENT DOCUMENTS

| | | | |
|---|---|---|---|
| 8,696,820 B2 | 4/2014 | Vaillancourt et al. | |
| 8,740,864 B2 | 6/2014 | Hoang et al. | |
| 9,039,989 B2 | 5/2015 | Liu et al. | |
| 9,283,369 B2 | 3/2016 | Ma et al. | |
| 9,399,125 B2 | 7/2016 | Burkholz | |
| 9,480,833 B2 | 11/2016 | Hoang et al. | |
| D834,187 S | 11/2018 | Ryan | |
| 10,376,686 B2 | 8/2019 | Burkholz et al. | |
| 10,413,716 B2 | 9/2019 | Sathe | |
| 10,751,252 B2 | 8/2020 | Carrel et al. | |
| 10,871,246 B2 | 12/2020 | Marici et al. | |
| 11,083,883 B2 | 8/2021 | Ryan et al. | |
| 11,273,298 B2 | 3/2022 | Erekovcanski et al. | |
| 11,344,715 B2 | 5/2022 | Erekovcanski et al. | |
| 11,353,147 B2 | 6/2022 | Marici et al. | |
| 11,389,636 B2 | 7/2022 | Coyle | |
| 2010/0050351 A1* | 3/2010 | Colantonio | A61M 39/20 |
| | | | 15/104.93 |
| 2012/0302968 A1 | 11/2012 | Tennican | |
| 2012/0302997 A1 | 11/2012 | Gardner et al. | |
| 2013/0035667 A1 | 2/2013 | Anderson et al. | |
| 2013/0178804 A1 | 7/2013 | Tennican | |
| 2013/0197485 A1 | 8/2013 | Gardner et al. | |
| 2014/0135739 A1 | 5/2014 | Solomon et al. | |
| 2015/0005699 A1 | 1/2015 | Burbank et al. | |
| 2015/0086441 A1 | 3/2015 | She et al. | |
| 2016/0106968 A1 | 4/2016 | Solomon et al. | |
| 2016/0144118 A1 | 5/2016 | Solomon et al. | |
| 2016/0310720 A1 | 10/2016 | Solomon et al. | |
| 2018/0055962 A1 | 3/2018 | Drmanovic | |
| 2018/0064604 A1 | 3/2018 | Drmanovic | |
| 2018/0071508 A1 | 3/2018 | Drmanovic | |
| 2018/0085568 A1 | 3/2018 | Drmanovic | |
| 2018/0200500 A1 | 7/2018 | Ziebol et al. | |
| 2018/0214242 A1 | 8/2018 | Davis et al. | |
| 2018/0214684 A1 | 8/2018 | Avula et al. | |
| 2018/0250194 A1 | 9/2018 | Drmanovic | |
| 2018/0256804 A1 | 9/2018 | Burbank et al. | |
| 2018/0256880 A1 | 9/2018 | Follman et al. | |
| 2018/0256881 A1 | 9/2018 | Hitchcock et al. | |
| 2018/0256883 A1 | 9/2018 | Follman et al. | |
| 2018/0369562 A1 | 12/2018 | Gardner et al. | |
| 2019/0038888 A1 | 2/2019 | Gardner | |
| 2019/0099593 A1 | 4/2019 | Avula et al. | |
| 2019/0117332 A1 | 4/2019 | Davis et al. | |
| 2019/0201681 A1 | 7/2019 | Ziebol et al. | |
| 2019/0262525 A1 | 8/2019 | Wyeth et al. | |
| 2019/0282795 A1 | 9/2019 | Fangrow | |
| 2019/0351212 A1 | 11/2019 | Dudar et al. | |
| 2020/0121858 A1 | 4/2020 | Anderson et al. | |
| 2020/0139037 A1 | 5/2020 | Ziebol et al. | |
| 2020/0155794 A1 | 5/2020 | Ziebol | |
| 2020/0197686 A1 | 6/2020 | Anderson et al. | |
| 2020/0238070 A1 | 7/2020 | Ryan | |
| 2021/0001110 A1 | 1/2021 | Bedoe et al. | |
| 2021/0008283 A1 | 1/2021 | San Solo et al. | |
| 2021/0093791 A1 | 4/2021 | Anderson et al. | |
| 2021/0138225 A1* | 5/2021 | Jiang | A61M 39/20 |
| 2021/0154462 A1* | 5/2021 | Drmanovic | A61M 39/165 |
| 2021/0275707 A1 | 9/2021 | Jiang et al. | |
| 2021/0322749 A1* | 10/2021 | Rothenberg | A61M 39/1011 |
| 2021/0322750 A1 | 10/2021 | Harandi et al. | |
| 2021/0322751 A1 | 10/2021 | Jiang et al. | |
| 2021/0322752 A1 | 10/2021 | Jiang et al. | |
| 2022/0273881 A1 | 9/2022 | Mahmoodian et al. | |
| 2023/0240669 A1 | 8/2023 | Wight et al. | |

* cited by examiner

DISINFECTING CAP FOR MALE AND FEMALE CONNECTORS INCLUDING A CONSTRICTING LOCK

BACKGROUND OF THE INVENTION

Field of the Invention

The present disclosure relates generally to caps for medical connectors and, in particular, to a medical cap configured to be attached to either a male connector or a female connector for sealing, cleaning, and disinfecting portions of the connector.

Description of Related Art

Vascular access devices (VADs) are commonly used medical devices, which can include intravenous (IV) catheters, such as peripheral catheters or central venous catheters. If not properly maintained or if exposed to a non-sterile environment, the VADs can become contaminated, sealed with blood clots, and/or can spread infection. Further, bacteria and other microorganisms may enter into a patient's vascular system from access hubs, ports, or valves upon connection to the VAD to deliver a fluid or pharmaceutical to a patient. Therefore, each access hub, port, valve, or other connection configured for attachment to a VAD is associated with some risk of transmitting a catheter related bloodstream infection (CRBSI) to a patient.

Many medical facilities implement sterile practices and protocols to ensure that VADs and access hubs or ports are used properly and do not become sealed or infected. These protocols often include sterilizing the access hubs, ports, and VADs, as well as flushing the catheter with a flush solution prior to use. Specifically, VAD standards of practice usually recommend flush procedures be performed after catheter placement, before fluid infusion, and before and after drug administration, blood sampling, transfusions, and/or administration of parenteral nutrition. Standards of practice can also require that access hubs, ports, and valves be capped with disinfection caps when not in use, to prevent microbial ingress into the hub, port, or valve and to sterilize areas of the hub, port, or valve that contact the VAD. Disinfection caps are disposable cap devices that contain an amount of cleaning or disinfecting solution for sterilizing portions of the port, hub, and valve.

Access hubs and ports can have a variety of different types of male or female connectors for securing the hub or port to the VAD. Currently, practitioners often carry several types of caps with them so that they can cap different types of hubs and ports, which may all be used for a particular patient. For example, caps for male needleless connectors and female needleless connectors, as well as intravenous (IV) and hemodialysis lines, often use different connector designs and may require different caps. There can be "male disinfecting cap devices" for disinfecting ISO594-2 type of female threaded fluid luer connectors and "female disinfecting cap devices" for disinfecting ISO594-2 type of male threaded fluid luer connectors.

Some examples of universal caps that fit on both male and female connectors are known. For example, U.S. Pat. No. 10,871,246, entitled "Universal connector or cap for male and female threaded fittings," which is incorporated herein by reference in its entirety, discloses a cap including a threaded protrusion that can engage both a male connector and a female connector. However, there is a need for simpler cap designs that can be manufactured inexpensively and efficiently. The universal caps of the present disclosure are configured to attach to both male and female medical connectors in a secure manner sufficient for preventing microbial ingress. Further, the universal caps of the present disclosure are configured to be easy to manufacture in a single-molding process.

SUMMARY OF THE INVENTION

According to an aspect of the disclosure, a cap configured to engage at least a first connector and a second connector of different types includes a housing having a an open first end, a second end, at least one sidewall extending between the first end and the second end, and at least one opening extending through the at least one sidewall. The cap further includes a flexible sleeve disposed in the housing having a first end, a second end, and a sleeve sidewall extending between the first end and the second end. The cap further includes a lock connected to the housing configured to move through the at least one opening of the housing to press against the sleeve sidewall, which causes the sleeve sidewall to directly or indirectly press against a portion of the first connector or the second connector to secure the first connector or the second connector in the housing. The cap also includes an absorbent member disposed in the flexible sleeve configured to contain a cleaning solution for cleaning and/or disinfecting portions of the first connector or the second connector engaged to the cap.

In accordance with an embodiment of the present invention, the first connector is a female connector and the second connector is a male connector.

In accordance with an embodiment of the present invention, the cap is sized to receive male and/or female connectors having different thread configurations and dimensions.

In accordance with an embodiment of the present invention, the cap is sized to receive female connectors having threads with a width at a crest of from about 0.3 mm to about 1.0 mm and a width at a root of the crest from about 0.5 mm to 1.2 mm.

In accordance with an embodiment of the present invention, the first connector includes a female luer connector and the second connector includes a male luer connector.

In accordance with an embodiment of the present invention, an inner surface of the flexible sleeve is a cylindrical surface without threads or grooves.

In accordance with an embodiment of the present invention, the absorbent member is configured to clean and/or disinfect threaded surfaces of the first connector or the second connector.

In accordance with an embodiment of the present invention, the lock is configured to connect to the housing to hold the lock against the flexible sleeve, thereby securing the first connector or the second connector in the housing.

In accordance with an embodiment of the present invention, a first portion of the lock is rotatably connected to the housing so that the lock rotates about the first portion towards the flexible sleeve in a first direction, and wherein a second portion of the lock connects to the housing to prevent the lock from rotating in a second direction away from the flexible sleeve.

In accordance with an embodiment of the present invention, the housing and lock include a rigid thermoplastic polymer having at least one of polyester, polycarbonate, polypropylene, polyethylene, polyethylene terephthalate, or acrylonitrile butadiene styrene.

In accordance with an embodiment of the present invention, the housing further includes a tab, and wherein the lock is rotatably, slideably, and/or pivotally connected to the tab.

In accordance with an embodiment of the present invention, the housing includes a plurality of ridges or ribs extending outwardly from an outer surface of the housing (for making the housing easier to grip).

In accordance with an embodiment of the present invention, the flexible sleeve includes a thermoplastic elastomer having at least one of silicone, polypropylene, polyethylene, or synthetic or natural rubber (e.g., isoprene).

In accordance with an embodiment of the present invention, an outer diameter of the flexible sleeve substantially matches an inner diameter of the housing.

In accordance with an embodiment of the present invention, the first end of the sleeve includes an opening and a flange extending about the opening, and wherein the flange rests against the open first end of the housing.

In accordance with an embodiment of the present invention, the lock causes the sleeve to deform radially inwardly to directly or indirectly contact the portion of the first connector or the second connector.

In accordance with an embodiment of the present invention, the first end of the sleeve is open and the second end of the sleeve is closed.

In accordance with an embodiment of the present invention, an inner diameter of the flexible sleeve is greater than a maximum outer diameter of the first connector or the second connector, such that the flexible sleeve does not restrict insertion of the first connector or the second connector into the housing.

In accordance with an embodiment of the present invention, the housing further includes a tab.

In accordance with an embodiment of the present invention, the lock is rotatably engaged to the tab, such that the lock rotates relative to the tab to press against the flexible sleeve.

In accordance with an embodiment of the present invention, the tab of the housing further includes a slot and wherein a portion of the lock inserts into the slot to hold the lock in contact with the flexible sleeve.

In accordance with an embodiment of the present invention, the lock includes a proximal end that is connected to the tab of the housing, a distal end opposite the proximal end, and a cam portion between the proximal end and the distal end of the lock.

In accordance with an embodiment of the present invention, the cam portion includes a concave inner surface and a convex outer surface, and wherein rotation of the lock relative to the housing causes the convex outer surface of the cam portion to contact the flexible sleeve.

In accordance with an embodiment of the present invention, the distal end of the lock includes a handle configured to be grasped by a user to rotate the lock towards the flexible sleeve.

In accordance with an embodiment of the present invention, the proximal end of the lock includes a proximal post configured to be inserted in a hole in the tab of the housing thereby forming a rotation point for rotation of the lock relative to the housing.

In accordance with an embodiment of the present invention, the distal end of the lock includes a distal post extending therefrom configured to be inserted into a slot extending through the tab of the housing for holding the lock in a position pressing against the flexible sleeve.

In accordance with an embodiment of the present invention, rotating the lock about the rotation point moves the distal post through the slot and increases pressure against the flexible sleeve.

In accordance with an embodiment of the present invention, the slot includes a plurality of protrusions configured to engage the distal post to hold the lock in a selected position relative to the flexible sleeve.

In accordance with an embodiment of the present invention, the lock applies a variable pressing force to the sleeve, which increases proportionally as an angle of rotation of the lock relative to the housing increases.

In accordance with an embodiment of the present invention, the lock is at least one of slidably, pivotally, or rotatably connected to the housing.

In accordance with an embodiment of the present invention, a pressing force of the lock against the flexible sleeve causes the first connector or the second connector to be retained within the flexible sleeve in a position where a longitudinal axis of the connector is offset from a longitudinal axis of the housing of the cap.

In accordance with an embodiment of the present invention, a seal is disposed in the housing over the absorbent member to clean and disinfect the first connecter or the second connector as the first connector or the second connector is inserted into the housing.

In accordance with an embodiment of the present invention, a seal includes a non-porous foam, such as a closed cell foam.

In accordance with an embodiment of the present invention, the absorbent member includes a sponge.

In accordance with an embodiment of the present invention, the absorbent member includes an open cell foam, such as a porous foam having a thermoplastic elastomer.

In accordance with an embodiment of the present invention, insertion of the first connector or the second connector into the housing causes the absorbent member to axially compress.

In accordance with an embodiment of the present invention, axial compression of the absorbent member causes the cleaning solution of the absorbent member to contact threads and surfaces of the first connector or the second connector.

In accordance with an embodiment of the present invention, the cleaning solution is absorbed by the absorbent support.

In accordance with an embodiment of the present invention, the cleaning solution includes Isopropyl Alcohol (IPA).

In accordance with an embodiment of the present invention, the cleaning solution includes from about 0.5% to about 3.5% chlorhexidine gluconate and about 70% IPA In accordance with an embodiment of the present invention, a protective covers over the open first end of the housing.

In accordance with an embodiment of the present invention, the protective cover is attached to the housing by heat scaling.

In accordance with an embodiment of the present invention, a flange extends about an opening of the first end of the flexible sleeve is positioned between the cover and the open first end of the housing.

According to another aspect of the disclosure, a method for attaching the previously described cap to the first connector or the second connector includes inserting a distal end of the first connector or the second connector through the open first end of the housing and the first end of the flexible sleeve. The method also includes applying axial pressure to the connector causing the absorbent member to axially compress and moving the distal end of the connector farther into the flexible sleeve; and moving a portion of the lock through the at least one opening of the at least sidewall of the housing, thereby pressing the flexible sleeve directly or indirectly against the connector to retain the connector within the housing.

In accordance with an embodiment of the present invention, the method further includes inserting a distal end of the first connector or the second connector through the open first end of the housing and the first end of the flexible sleeve, and applying axial pressure to the connector causing the absorbent member to axially compress and moving the distal end of the connector farther into the flexible sleeve; and moving a portion of the lock through the at least one opening of the at least sidewall of the housing, thereby pressing the flexible sleeve directly or indirectly against the connector to retain the connector within the housing.

In accordance with an embodiment of the present invention, inserting the connector into the housing includes inserting the connector through the open first end of the housing and first end of the flexible sleeve without twisting or rotating the connector relative to the flexible sleeve.

In accordance with an embodiment of the present invention, the first connector is a female connector and the second connector is a male connector.

In accordance with an embodiment of the present invention, the housing further includes a tab, and wherein the lock is rotatably engaged to the tab, such that the lock rotates relative to the tab to press against the flexible sleeve.

In accordance with an embodiment of the present invention, the tab of the housing further includes a slot and wherein a portion of the lock inserts into the slot to hold the lock in contact with the flexible sleeve.

In accordance with an embodiment of the present invention, the lock includes a proximal end that is connected to the tab of the housing, a distal end opposite the proximal end, and a cam portion between the proximal end and the distal end of the lock.

In accordance with an embodiment of the present invention, the distal end of the lock includes a handle configured to be grasped by a user, and wherein the user grasps the handle to move the lock through the at least one opening of the at least one sidewall of the housing.

In accordance with an embodiment of the present invention, the distal end of the lock includes a distal post extending therefrom, and the method further includes inserting the distal post of the lock into the slot of the tab to hold the lock in a position pressing against the flexible sleeve.

In accordance with an embodiment of the present invention, the method further includes removing a protective cover positioned over the open first end of the housing from the housing prior to inserting the distal end of the first connector or the second connector through the open first end of the housing.

According to another aspect of the disclosure, a cap includes a housing having an open first end, a second end, at least one sidewall extending between the first end and the second end, at least one opening extending through the at least one sidewall, and a tab extending outward from the at least one sidewall of the housing. The tab includes a hole and a slot. The cap also includes a flexible sleeve disposed in the housing having a first end, a second end, and a sleeve sidewall extending between the second end and the first end, and a lock. The lock includes (i) a proximal post inserted into the hole of the tab providing a rotation engagement between the lock and the tab, and (ii) a distal post configured to insert into the slot of the tab preventing rotation of the lock relative to the tab. The cap also includes an absorbent member disposed in the flexible sleeve configured to contain a cleaning solution for cleaning and/or disinfecting portions of the first connector or the second connector engaged to the cap.

In accordance with an embodiment of the present invention, the cap is configured to receive a connector and wherein, with the connector inserted into the housing, moving the lock in a first direction causes the lock to press against the flexible sleeve, which secures the connector to the housing.

In accordance with an embodiment of the present invention, the cap is configured to receive different types of connectors, such as a male connector and a female connector.

In accordance with an embodiment of the present invention, the cap is configured to receive connectors of different sizes and thread configurations.

In accordance with an embodiment of the present invention, the lock includes a proximal end having the proximal post, a distal end opposite the proximal end comprising the distal post, and a cam portion between the proximal end and the distal end of the lock.

In accordance with an embodiment of the present invention, the cam portion includes a concave inner surface and a convex outer surface, and wherein rotation of the lock relative to the housing causes the convex outer surface of the cam portion to contact the flexible sleeve.

In accordance with an embodiment of the present invention, the distal end of the lock includes a handle configured to be grasped by a user to rotate the lock towards the flexible sleeve.

In accordance with an embodiment of the present invention, the slot includes a plurality of protrusions configured to engage the distal post to hold the lock in a selected position relative to the flexible sleeve.

DESCRIPTION OF THE INVENTION

Figure 1B:
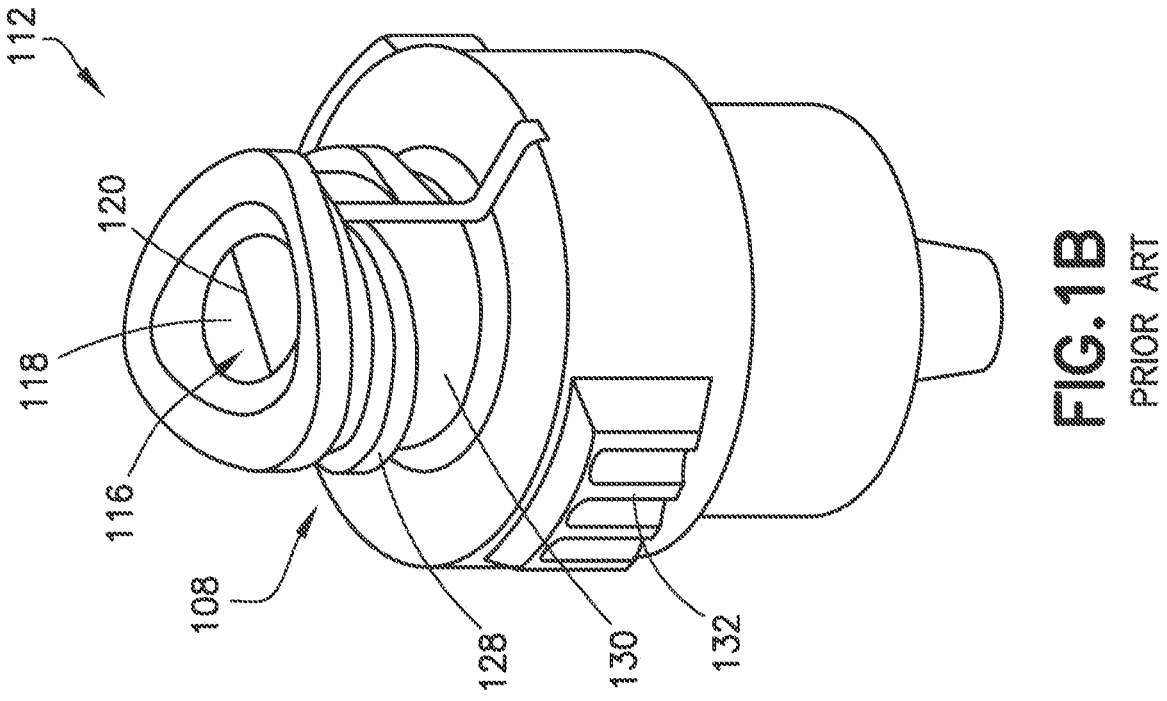
FIG. 1B is an example of a closed female connector including a septum with a slit, as is known in the prior art.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. The term "proximal" refers to a portion of a device or part that is grasped by a user or connected to another device or part. The term "distal" refers to a portion of a device or part that is opposite the proximal portion (i.e., farthest away from the portion that is grasped by a user or connected to another part). For example, for an implantable medical device, such as a catheter, a proximal portion can refer to the portion of the catheter that remains outside of a patient's body and is manipulated by a user. The distal portion of the catheter can be the portion that is inserted into the vasculature of the patient. For an object or part, such as an elongated member, the proximal end can be the end that is connected to another object or part. The distal end of the elongated member is opposite the proximal end and can be free from connections to other objects or parts. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The present disclosure is directed to a cap 10 configured to be connected to a medical connector 110, 112, such as an access hub, port, or valve for a VAD, to prevent the connector, port, or VAD from being contaminated by, for example, microbes, debris, or other contaminants. In some examples, the cap 10 can be configured to clean or disinfect portions of the connector 110, 112 or port, ensuring that the connector 110, 112 or port remains sterile prior to use. The cap 10 can be configured to remain in place on a connector 110, 112 or port for at least seven days, which is a maximum time of recommended use permitted by many medical facility sterile practice guidelines.

Figure 1A:
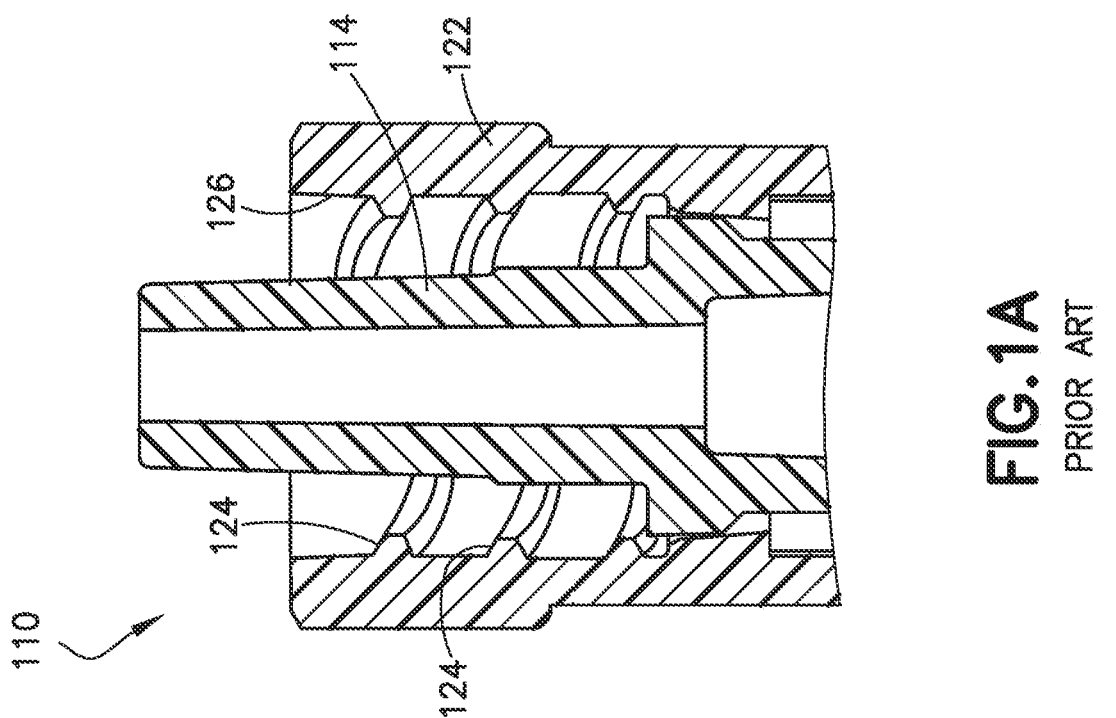
FIG. 1A is a cross-sectional view of an exemplary male connector, as is known in the prior art.

The cap 10 is a universal cap meaning that it is configured to engage with or be connected to different sizes, configurations, and/or types of medical connectors 110, 112. For example, the cap 10 can be configured to engage with or be connected to both a male connector 110 and a female connector 112. As used herein, a "male connector" refers to a connector 110 comprising an elongated member, such as a tubular member or stem 114, configured to be inserted in a tube or opening having an inner diameter that is larger than an outermost diameter of the male connector 110. An exemplary male connector 110 is shown in FIG. 1A. By contrast, a "female connector" refers to a connector 112 comprising an opening or port 116 that is configured to receive an elongated member or tubular member of another object or device in order to connect the object or device to the female connector 112. The female connector 112 can comprise an elongated distal end portion 108 with a cover or septum 118 over the opening 116. An exemplary female connector 112 including a septum 118 with a slit 120 is shown in FIG. 1B.

In some examples, the cap 10 is configured to engage different types of luer connectors, such both a male luer connector 110 and a female luer connector 112. For example, the cap 10 can be an appropriate size to receive a female luer connector 112 having an outer diameter of about 7.0 mm to about 8.0 mm. The cap 10 can also be sized to receive a male luer connector 110 having an outer diameter of from about 8.0 mm to about 12.0 mm.

As used herein, a "luer connector" refers to a connector that includes a tapered portion (i.e., a luer taper) for creating a friction engagement between a tapered stem 114 or elongated member of a male luer connector 110 and a tapered cavity. For example, the male luer connector 110 can include a tapered stem 114 or elongated member having a tapered outer surface. The female luer connector 112 can include a tapered cavity configured to receive and engage the tapered stem 114 or elongated member to connect the male luer connector 110 to the female luer connector 112.

In some examples, the male connectors 110 and the female connectors 112 can include engaging structures, such as threads, for drawing the connectors 110, 112 to another connector or port. For example, as shown in FIG. 1A, the male luer connector 110 can include an annular shield 122 extending about the tapered stem 114 or elongated member. The annular shield 122 can include threads 124 on an inner surface 126 of the shield 122 configured to engage corresponding threads 128 on an outer surface 130 of the female luer connector 112. As shown in FIG. 1B, the female luer connector 112 includes the threads 128 extending from the outer surface 130 positioned to engage the threads 124 on the inner surface 126 of the annular shield 122 of the male luer connector 110. Twisting the female connector 112 relative to the male connector 110 causes the corresponding threads 124, 128 to engage, which draws the connectors 110, 112 together, such that the tapered stem 114 or elongated member of the male luer connector 110 moves through the opening 116 of the female connector 112. In some examples, the female connector 112 can also include vertical ribs 132 near a proximal end of the female connector 112, which can be used to manipulate the female connector 112 making it easier to twist the female connector 112 relative to another connector or device.

There are numerous commercially available medical devices, such as hubs, ports, and valves, which include different variations of male or female connectors 110, 112, such as male and female luer connectors. As described in further detail herein, the cap 10 of the present disclosure includes a flexible sleeve, which can be constricted by a lock, in order to engage and securely connect to different types and sizes of connectors 110, 112. For example, the cap 10 can be configured to attach to both male and female luer connectors 110, 112, such as male or female Luer-Lok™ connectors by Becton Dickinson and Company. The cap 10 can also be configured to cover different connector designs including, without limitation, the BD Q-Syte™, BD MaxZero™, BD MaxPlus™, and SmartSite™ needle free connectors by Becton Dickinson and Company. The cap 10 can also be configured to be connected to male and/or female connectors by other manufactures including, without limitation, MicroClave® connectors (ICU Medical Inc.) and Ultrasite® connectors (B. Braun Medical Inc.). In other examples, the cap 10 can be configured to be connect to one or more of the following commercially available male connectors: Kendall 2001NP; BD MP5303-C; ICU Med 12664-28; RyMed RYM-5307HPU; B. Braun 470108; Baxter 2C8537; Kawasumi IV-0094; Zyno B2-70071-D; B. Braun 470124; Baxter 2C7462; and Smith's Medical 536035.

Universal Cap for Male and Female Connectors

Figure 2A:
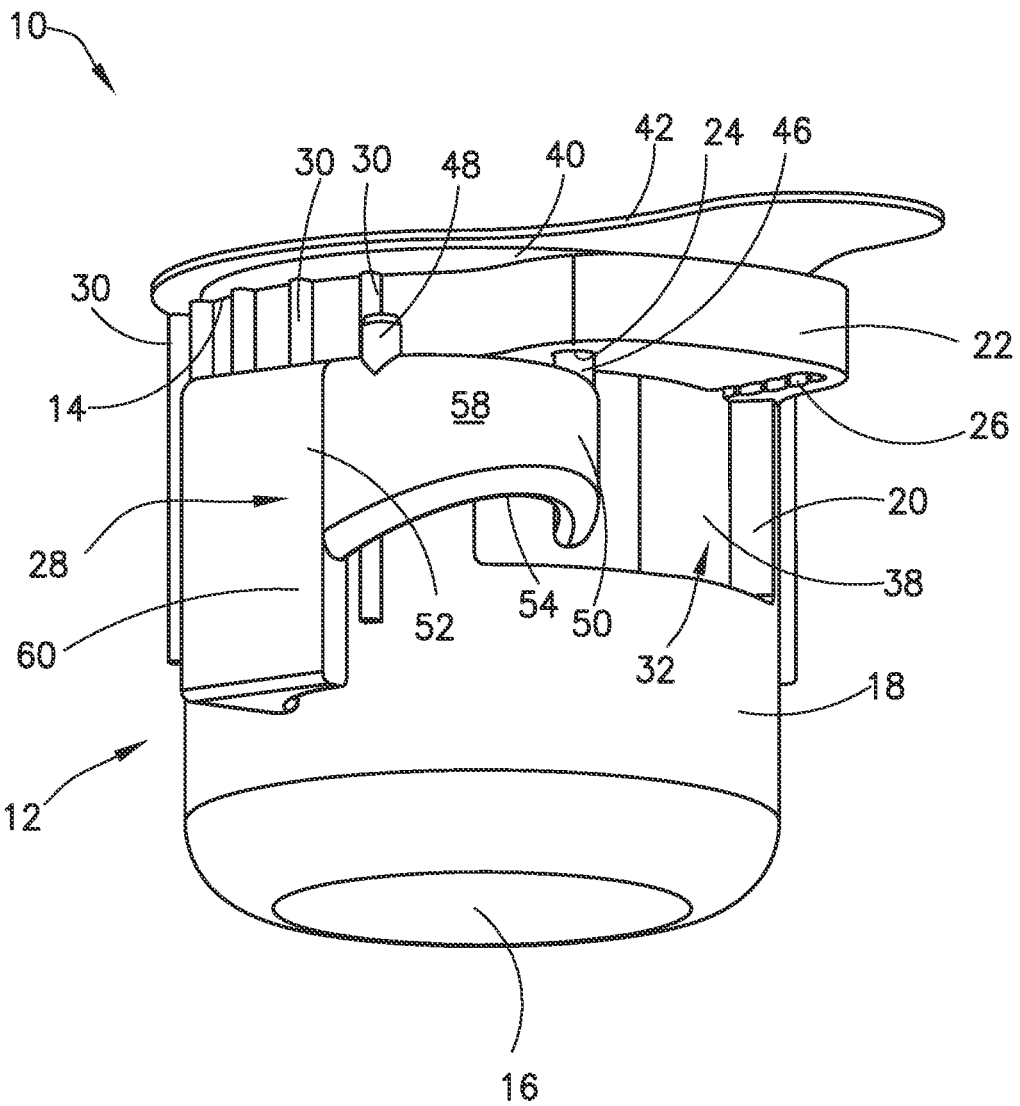
FIG. 2A is a perspective view of a universal cap with a lock of the cap in an open position, according to an aspect of the present disclosure.
Figure 2B:
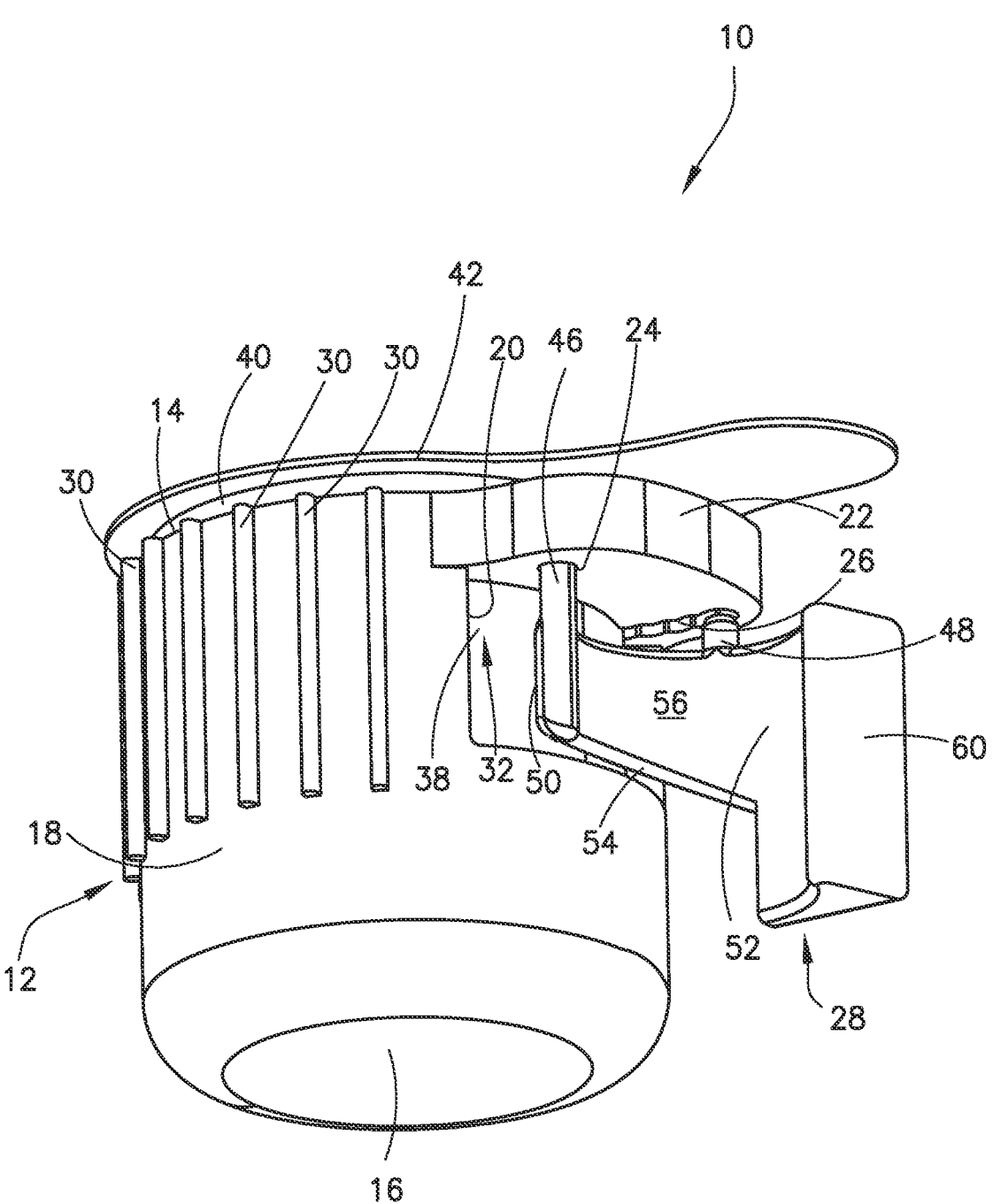
FIG. 2B is a perspective view of the cap of FIG. 2A with the lock in a closed position.
Figure 2C:
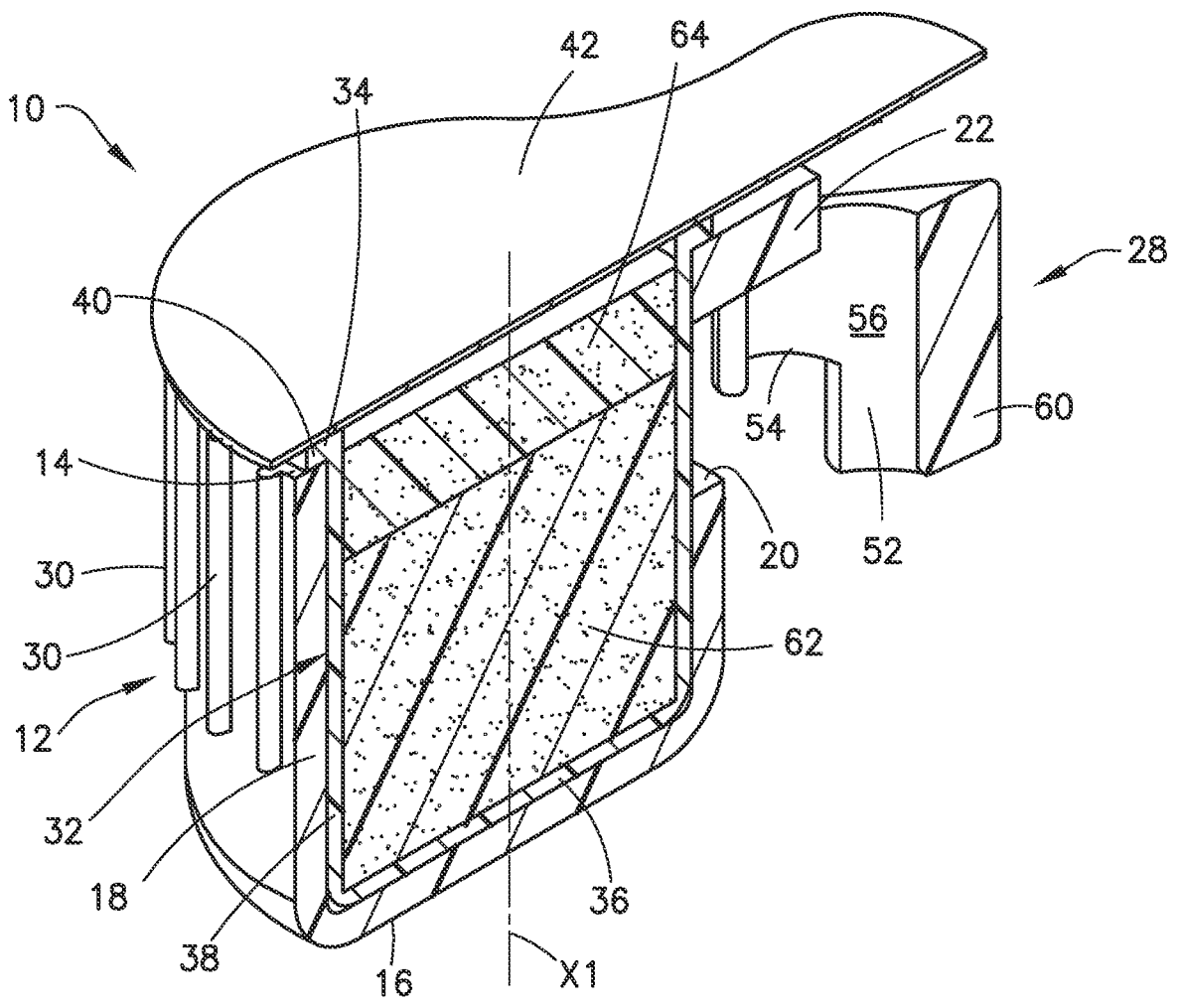
FIG. 2C is a perspective view of a cross section of the cap of FIG. 2A.
Figure 3:
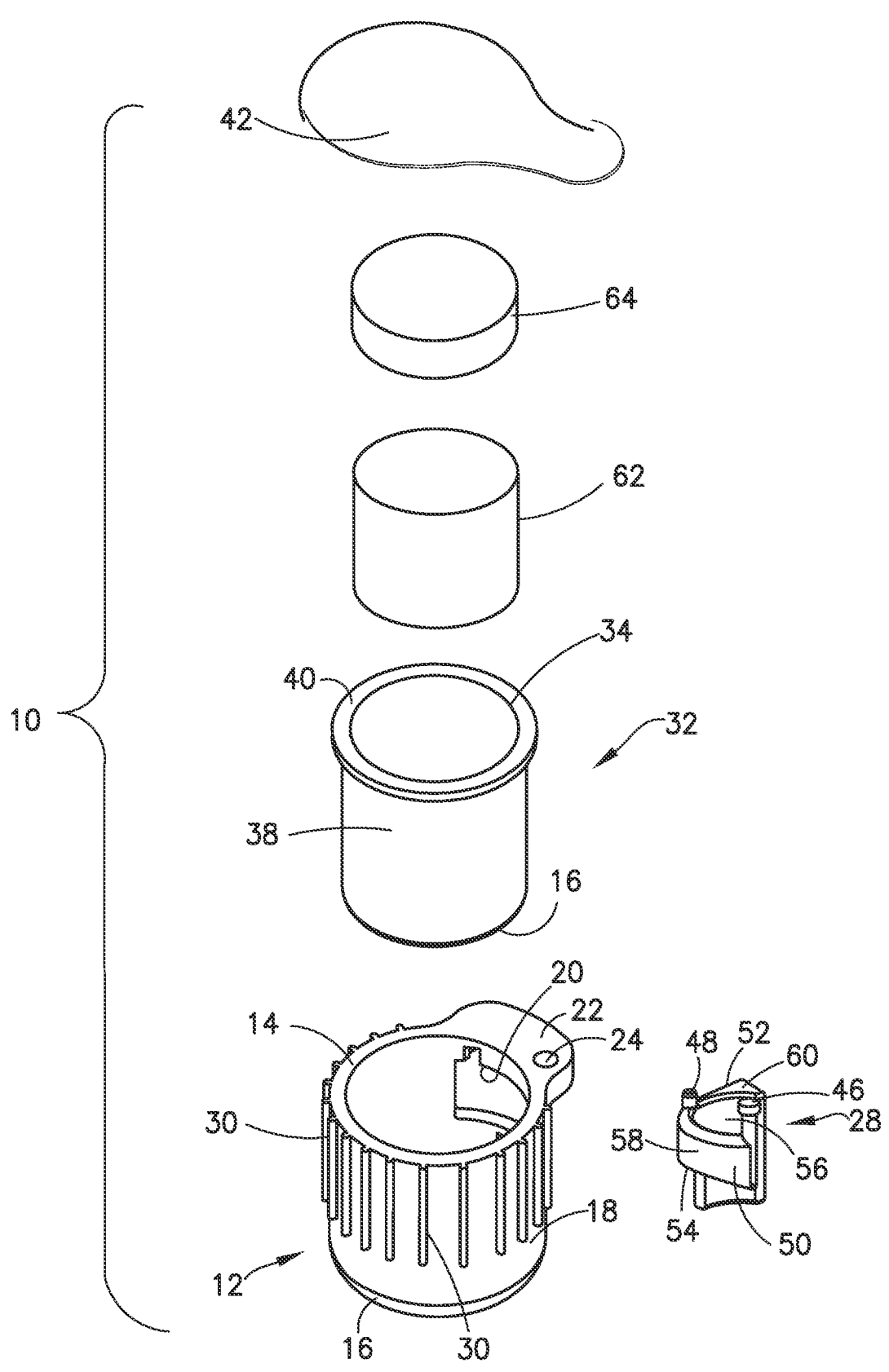
FIG. 3 is an exploded perspective view of the cap of FIG. 2A.
Figures 4A, 4B:
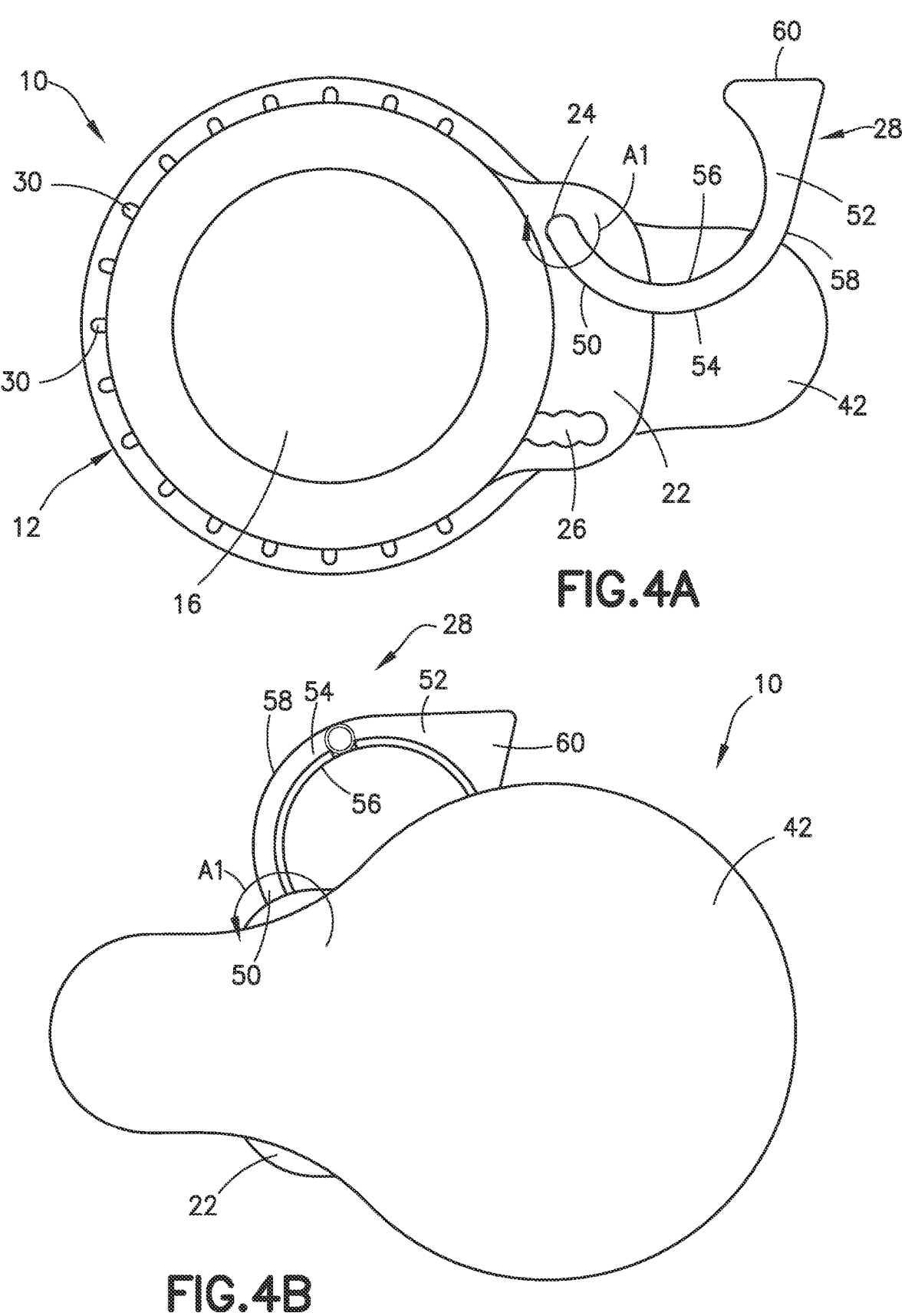
FIG. 4A is a bottom view of the cap of FIG. 2A with the lock in the open position.
FIG. 4B is a top view of the cap of FIG. 2A with the lock in the open position.
Figure 5A:
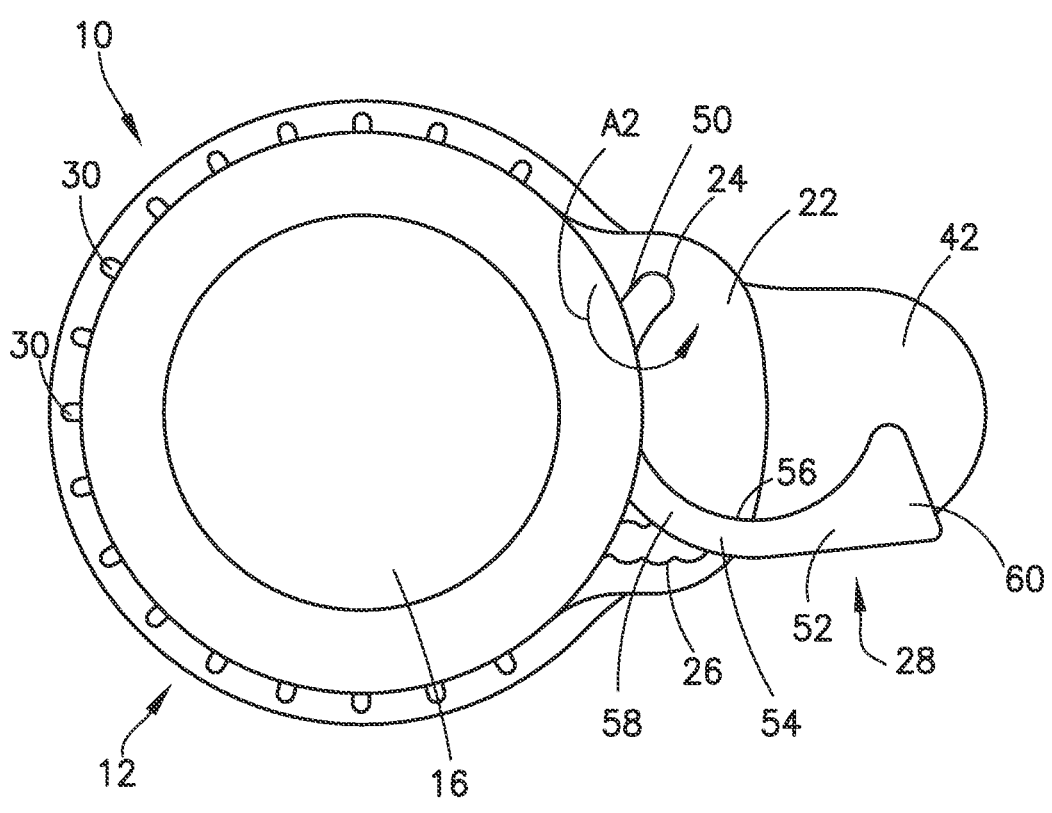
FIG. 5A is a bottom view of the cap of FIG. 2A with the lock in the closed position.
Figure 5B:
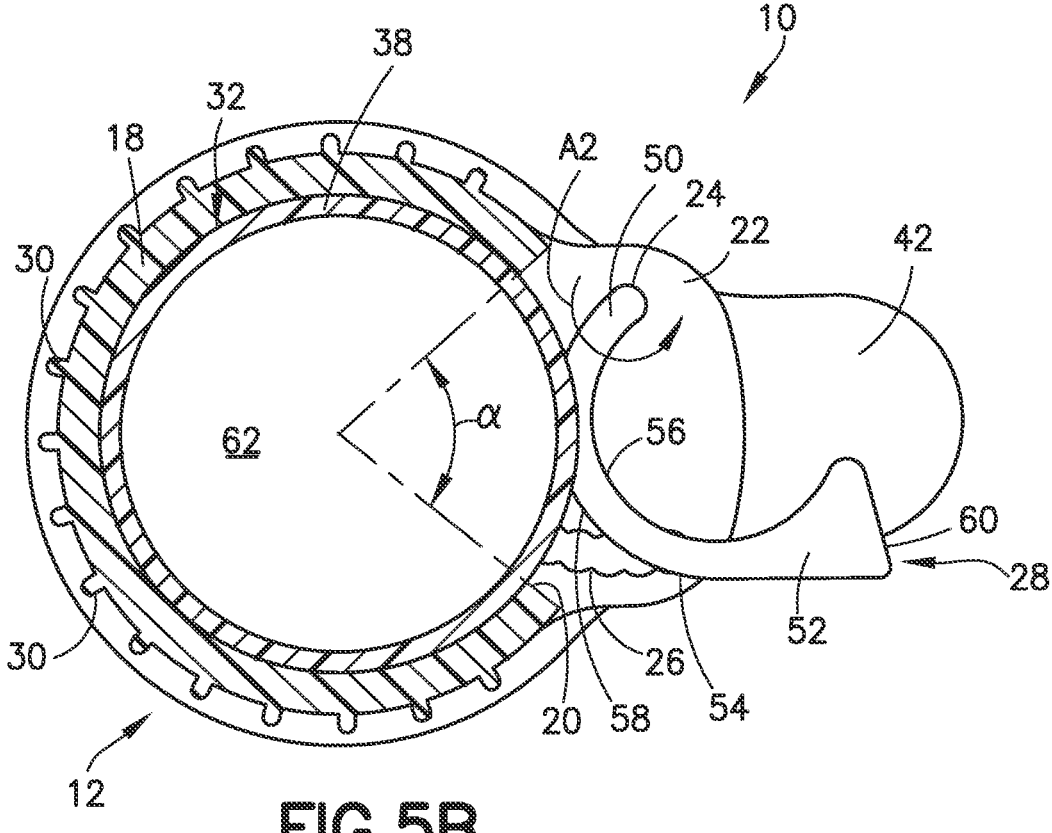
FIG. 5B is a cross-sectional view of the cap of FIG. 2A with the lock in the closed position.

FIGS. 2A-5B illustrate an exemplary universal cap 10 configured to engage and/or to be connected to different types of connectors, such as any of the previously described male connectors 110 and female connectors 112. Specifically, FIG. 2A is a perspective view of the cap 10 showing a lock of the cap 10 in an open position. FIG. 2B is a perspective view of the cap 10 with the lock in a closed position. FIG. 2C is a cross-sectional view of the cap 10 with the lock in the open position. FIG. 3 is an exploded view of the cap 10. FIGS. 4A and 4B are additional views showing the cap 10 with the lock in the open position. FIGS. 5A and 5B are additional views showing the cap 10 with the lock in the closed positon. In some examples, the cap 10 can be provided as a single pre-packaged cap or cap assembly, such as the packaged cap shown in FIGS. 2A-5B. Further, as described in further detail herein, the cap 10 includes components, such as sponges, abrasive surfaces, and/or cleaning or disinfecting solutions, for cleaning, scrubbing, and disinfecting portions of male and female connectors 110, 112 inserted into and mounted to the cap 10.

As shown in FIGS. 2A-5B, the cap 10 comprises a housing 12 comprising an open first end or top 14, a second or bottom 16, and a sidewall 18 extending between the top 14 and the bottom 16. The housing 12 further comprises an opening 20 extending through the sidewall 18 of the housing 12. For example, as shown in FIGS. 2A and 2B, the opening 20 can be a rectangular opening positioned between the top 14 and the bottom 16 of the housing 12. The rectangular opening 20 can have a long side extending along a circumference of the housing 12 and a short side extending axially (e.g., between the top 14 and the bottom 16 of the housing 12). As shown in FIG. 5B, the opening 20 can extend an angular distance (shown by angle α in FIG. 5B) of about 30 degrees to about 60 degrees. Other portions of the sidewall 18 of the housing 12 can be free from openings.

The housing 12 can further comprise an extension or tab 22 extending from the sidewall 18 of the housing 12. The tab 22 can be provided to make the cap 10 easier to hold or manipulate for a practitioner when using the cap 10. For example, a practitioner can grasp the tab 22 while removing packaging, covers, and other seals from the cap 10 prior to use. As described in further herein, the tab 22 can include a hole 24 and one or more slots 26, viewable on an underside of the tab 22 (shown in FIGS. 2A, 2B, 4A, and 5A) for securing a lock 28 or locking mechanism of the cap 10 to the housing 12. For example, the lock 28 can be rotatably, slideably, and/or pivotally connected to the tab 22.

In some examples, the housing 12 further comprises protrusions, such as axially extending ribs or ridges 30, extending outward from an outer surface of the sidewall 18 of the housing 12. The axial ridges 30 can be provided to increase rigidity of the housing 12 compared to if ridges 30 were not present. Also, the ridges 30 can make the housing 12 easier to grasp and manipulate improving usability of the cap 10 and, for example, making it less likely that the practitioner will drop or mishandle the cap 10 during use.

In some examples, the housing 12 is a molded part formed by injection molding or other common molding processes. The housing 12 can be formed from a thermoplastic polymer material, such as polyester, polycarbonate, polypropylene, polyethylene, polyethylene terephthalate, or acrylonitrile butadiene styrene. In some examples, the housing 12 can be formed from a durable material, such as a material having a shore hardness D value of less than or equal to 95 (Shore D). Alternatively, the housing 12 can be formed from a more flexible material, such as a material having a shore hardness A value less than or equal to 130 (Shore A).

The cap 10 further comprises a flexible sleeve 32 disposed in the housing 12 that is sized to receive the connectors 110, 112 and configured to be pressed or constricted against the connectors 110, 112 to secure the connectors 110, 112 in the housing 12. In some examples, an inner diameter of the flexible sleeve 32 can be greater than a maximum outer diameter of a distal portion of the connectors 110, 112, such that the flexible sleeve 32 does not restrict insertion of the connector 110, 112 into the housing 12 or otherwise contact the connector 110, 112 until the flexible sleeve 32 is constricted against the connector 110, 112 by the lock 28.

The flexible sleeve 32 can comprise a first end or top 34, a second end or bottom 36, and a sleeve sidewall 38 extending between the top 34 and the bottom 36. The flexible sleeve 32 can comprise or can be formed from a flexible material that is capable of being pressed radially inward constricting against the connector 110, 112. For example, the flexible sleeve 32 can be formed from silicone or another thermoplastic elastomer, such as polypropylene, polyethylene, or synthetic or natural rubber (e.g., isoprene).

In some examples, the flexible sleeve 32 is a tubular body having a closed bottom 36 configured to rest against the closed bottom 16 of the housing 12 and an open top 34. An outer diameter of the sleeve sidewall 32 can match (e.g., can be equal to or slightly smaller, such as about 5% smaller than) an inner diameter of the housing 12, such that the flexible sleeve 32 fits in the housing 12. The flexible sleeve 32 can define a cylindrical interior or cavity sized to receive a distal portion of the connector 110, 112. Further, the sleeve sidewall 38 can be cylindrical having a cylindrical inner surface and/or a cylindrical outer surface. The inner and/or outer surfaces of the sleeve sidewall 38 can be free from threads or grooves. Instead, as previously described, the connector 110, 112 is secured in the housing 12 because the flexible sleeve 32 is constricted about the connector 110, 112 by the lock 28. More specifically, as described in further detail herein, the connector 110, 112 is secured to the flexible sleeve 32 by a radially inwardly directed pressure applied against the flexible sleeve 32 by the lock 28. The flexible sleeve 32 is not connected to the connector 110, 112 by an engagement between threads of the connector 110, 112 and corresponding threads of the flexible sleeve 32 or housing 12.

In some examples, the top 34 of the flexible sleeve 32 includes an annular flange 40 extending radially outward from an opening at the top 34 of the flexible sleeve 32. As shown, for example, in FIG. 2C, the annular flange 40 rests against the open top 14 of the housing 12 creating space between the open top 14 of the housing 12 and packaging (such as a protective cover 42) provided over the open top 14 of the housing 12.

The cap 10 further comprises the lock 28 connected to the housing 12 configured to move through the opening 20 in the sidewall 18 of the housing 12 to press against the sleeve sidewall 38. The lock 28 can be engaged (e.g., rotatably, slideably, and/or pivotally engaged) or connected to the tab 22 of the housing 12 as shown most clearly in FIGS. 2A and 2B. The lock 28 can be configured to move from an open position (shown in FIG. 2A) to a closed position (shown in FIG. 2B), where the lock 28 presses against the flexible sleeve 32. In some examples, the lock 28 applies a variable pressing force to the flexible sleeve 32, which increases proportionally with an angle of rotation of the lock 28 relative to the tab 22 of the housing 12. Accordingly, the farther the lock 28 is rotated in a first direction (shown by arrow A1 in FIGS. 4A and 4B) the more tightly the connector 110, 112 is retained within the housing 12.

In some examples, the lock 28 is configured to be grasped and manipulated by the practitioner to move the lock 28 from the open position (FIG. 2A) to the closed position (FIG. 2B). For example, the practitioner can gasp and press the lock 28 causing the lock 28 to rotate, slide, and/or pivot towards the flexible sleeve 32. Pressure applied by the lock 28 to the sleeve sidewall 38 of the flexible sleeve 32 causes the sleeve sidewall 38 to directly or indirectly press against a portion of the connector (e.g., the male connector 110 or the female connector 112) to secure the connector 110, 112 in the housing 12. In some examples, an inner surface of the sleeve sidewall 38 directly contacts and presses against the connector 110, 112 to secure the connector 110, 112 in the housing 12. In other examples, the sleeve sidewall 38 can indirectly contact the connector 110, 112 through one or more intermediate structures. For example, the sleeve sidewall 38 can contact and press against intermediate sleeves, layers, tubes, parts, or other structures to apply pressure from the lock 28 to the connector 110, 112 through the sleeve sidewall 38.

As shown, for example, in FIG. 2B, the lock 28 applies a pressing force to only one side of the flexible sleeve 32. Therefore, the pressing force of the lock 28 against the flexible sleeve 32 can cause the connector 110, 112 to be retained within the flexible sleeve 32 in a non-concentric orientation. Specifically, the female connector 112 can be retained in the housing 12 in a position where a longitudinal axis X2 (shown in FIGS. 6A and 6B) of the female connector 112 is offset from a longitudinal axis X1 (shown in FIGS. 2C, 6A, and 6B) of the housing 12 of the cap 10.

In some examples, portions of the lock 28 can be configured to connect to the housing 12 to hold the lock 28 against the flexible sleeve 32 (i.e., to prevent the lock 28 from moving away from the flexible sleeve 32 until the lock 28 is released by the practitioner. For example, a first portion (such as a proximal post 46) of the lock 28 can be rotatably connected to the housing 12 so that the lock 28 rotates about the first portion (e.g., about the proximal post 46) towards the flexible sleeve 32 in the first direction (shown by the arrow A1 in FIGS. 4A and 4B). Further, a second portion (such as a distal post 48) of the lock 28 can connect to the housing 12 to prevent the lock 28 from rotating in a second direction (shown by arrow A2 in FIGS. 5A and 5B) away from the flexible sleeve 32.

In some examples, the lock 28 is a molded part, formed from a similar or same material as the housing 12. For example, the lock 28 can be formed from a thermoplastic polymer material, such as polyester, polycarbonate, polypropylene, polyethylene, polyethylene terephthalate, or acrylonitrile butadiene styrene. Further, the lock 28 can comprise a proximal end 50 comprising the proximal post 46 that is connected to the tab 22 of the housing 12. For example, the proximal post 46 of the lock 28 can be inserted into the hole 24 of the tab 22, such that the lock 28 rotates about the proximal post 46 towards or away from the flexible sleeve 32. The lock 28 can further comprise a distal end 52 comprising the distal post 48 opposite the proximal end 50 and a cam portion 54 between the proximal end 50 and the distal end 52 of the lock 28. The cam portion 54 can include a concave inner surface 56 and a convex outer surface 58. Rotation of the lock 28 (in the first direction shown by arrow A1 in FIGS. 4A and 4B) relative to the tab 22 causes the convex outer surface 58 of the cam portion 54 to contact the flexible sleeve 32. Desirably, a substantial area of the convex outer surface 58 (e.g., at least 25%, 50%, or 75% of a total area of the convex outer surface 58) contacts the flexible sleeve 32 distributing a locking force from the lock 28 over a substantial portion of the outer surface of the sleeve sidewall 38. Accordingly, the pressing force of the sleeve sidewall 32 against the connector 110, 112 is distributed over a substantial portion of the outer surface of the connector 110, 112. Distributing this pressing force over a substantial arca of the outer surface of the connector 110, 112 forms a secure connection between the connector 110, 112 and the cap 10 without crushing or deforming any particular portions or parts of the connector 110, 112.

The distal post 48 of the lock 28 can be configured to be inserted into the slot 26 of the tab 22 for holding the lock 28 in a position pressing against the flexible sleeve 32. Specifically, the practitioner can rotate the lock 28 towards the flexible sleeve 32 causing the cam portion 54 of the lock 28 to press against the flexible sleeve 32. Once the lock 28 applies sufficient pressure against the flexible sleeve 32 to secure the connector 110, 112 to the cap 10, the practitioner can push the lock 28 in an upward direction, which inserts the distal post 48 into the slot 26. Inserting the distal post 48 into the slot 26 secures the lock 28 in place preventing the lock 28 from rotating away from the flexible sleeve 32, which secures the connector 110, 112 in the housing 12. In some examples, the distal post 48 can be capable of sliding through the slot 26 in a first direction to tighten the lock 28 against the flexible sleeve 32. In such instances, the slot 26 can include protrusions that prevent the distal post 48 from moving through the slot 26 in a second direction in order to loosen the lock 28. To disengage the lock 28, the practitioner removes the distal post 48 from the slot 26, thereby releasing the lock from engagement with the flexible sleeve 32.

In other examples, as shown in the figures, the slot 26 includes protrusions that form segments or circular holes or openings. Each segment or circular opening can be sized to receive the distal post 48, preventing the distal post 48 from sliding through the slot 26 in any direction (i.e., preventing the distal post 48 from sliding through the slot 26 in the first direction to tighten the lock 28 or in the second direction to loosen the lock 28). In such instances, with the distal post 48 outside of the slot 26, the practitioner applies pressure to the lock 28 causing the lock to press against the flexible sleeve 32. Once the lock 28 is sufficiently tight, the practitioner moves the distal post 48 into the slot 26 to hold the lock 28 in position against the flexible sleeve 32. The practitioner releases the lock 28 by removing the distal post 48 from the slot 26.

In some examples, the distal end 52 of the lock 28 also includes a handle 60 configured to be grasped by the practitioner to rotate the lock 28 towards the flexible sleeve 32. For example, the handle 60 can include one or more flat pressing surfaces that can be manipulated by the practitioner to move the lock 28 from the open positon to the closed position. The handle 60 can be designed to be large enough to be easily grasped and manipulated by the practitioner using, for example, one finger pressing against the handle 60, two fingers pressing against the handle 60, one thumb pressing against the handle 60, and/or grasping the handle 60 between a finger and a thumb.

The cap 10 further comprises an absorber, absorbent member, or support structure (referred to herein as the absorbent member 62) for cleaning and disinfecting portions of the male and female connectors 110, 112 inserted into the cap 10, such as threaded surfaces (e.g., roots and crests of threads 124, 128) of the connectors 110, 112. In particular, the absorbent member 62 can be configured to clean and disinfect surfaces of the stem 114, as well as the inner surface 126 and threads 124 of the annular shield 122 of the male connector 110. The absorbent member 62 can also be configured to clean and disinfect portions of the distal end portion 108, opening or port 116, and septum 118 of the female connector 112.

As shown in FIG. 2C, the absorbent member 62 can be disposed and held within a cylindrical interior space or cavity defined by the flexible sleeve 32. For example, the absorbent member 62 can be held in place within the flexible sleeve 32 by a conventional adhesive or mechanical fastener. In other examples, the absorbent member 62 can be held in place in the flexible sleeve 32 by friction between an inner surface of the sleeve sidewall 38 and an outer surface of the absorbent member 62.

In some examples, the absorbent member 62 comprises or is formed from an absorbent material capable of absorbing a cleaning or disinfecting solution for cleaning and/or disinfecting portions of the male connector 110 and the female connector 112. Further, the absorbent member 62 can be configured to axially compress as the distal portion of the connector 110, 112 is inserted into the housing 12 and the flexible sleeve 32. The axial compression of the absorbent member 62 can cause the cleaning solution of the absorbent member 62 to flow away from the absorbent member 62 and to contact the thread and other surfaces of the connector 110, 112 for cleaning and disinfecting portions of the connector 110, 112.

In some examples, the absorbent member 62 can comprise a thermoplastic elastomer, such as polypropylene, polyethylene, or synthetic or natural rubber (e.g., isoprene). The absorbent member 62 can also comprise a porous foam (e.g., an open cell foam) or sponge capable of absorbing the cleaning or disinfecting solution, such as a foam or sponge comprising polyurethane. In other examples, the foam material can be a Plastazote® foam, which is an engineered polymer foam by Zotefoams PCL.

In some examples, a height of the absorbent member 62 and/or amount of cleaning or disinfecting solution contained therein can be optimized for use with both short and tall connectors 110, 112. As used herein, a "short connector" refers to a connector 110, 112 that does not insert very far into the cap 10. By contrast, a "tall connector" refers to a connector that inserts into the cap 10 by a substantial distance, such that a distal end of the connector 110, 112 is proximate to the bottom 36 of the flexible sleeve 32. In particular, the height of the absorbent member 62 and amount of cleaning or disinfecting solution contained therein should be large enough so that sufficient cleaning solution is released from the absorbent member 62 when the cap 10 is attached to a short connector to disinfect surfaces of the short connector. However, the height of the absorbent member 62 and amount of cleaning solution may be somewhat limited so that liquid ingress into a lumen of the connector 110, 112 does not occur when the cap 10 is attached to a taller connector, which axially compresses the absorbent member 62 by a substantial amount.

The absorbent member 62 can be provided (i.e., presoaked) with the cleaning or disinfecting solution. For example, the cleaning or disinfecting solution can be an antimicrobial, anti-fungal, antibacterial, or antiviral solution that cleans and sterilizes surfaces of the connectors 110, 112.

In some examples, the cleaning solution can be isopropyl alcohol (IPA), such as about 70% IPA. In other examples, the cleaning solution can be about 0.5% to about 3.5% chlorhexidine gluconate in combination with about 70% IPA. A chlorhexidine composition may be beneficial because it has a slower evaporation rate than IPA and, therefore, provides a more persistent disinfectant activity after the cap 10 is removed from the connector 110, 112 and before the VAD is connected to the hub, port, or valve.

In some examples, the cap 10 further comprises a seal 64 positioned over the absorbent member 62 (e.g., positioned between a top of the absorbent member 62 and the top 34 of the flexible sleeve 32). The seal 64 can prevent fluids, such as cleaning or disinfecting solution in the cap 10, from flowing into the lumen of the male luer connector 110, when the male connector 110 is inserted into the cap 10. In some examples, the seal 64 can be formed from a thermoplastic elastomer comprising, for example, an elastomeric closed cell foam. Also, the seal 64 can comprise an abrasive material that is capable of scrubbing or mechanically removing objects, such as microbes and debris, from surfaces of the connectors 110, 112, while, at the same time, limiting ingress of cleaning or disinfecting solution into portions of the connectors 110, 112.

In some examples, the cap 10 can further comprise a removable and/or disposable protective cover 42 positioned over the open top 14 of the housing 12 and/or the top 34 of the flexible sleeve 32. For example, as shown in FIG. 2C, the protective cover 42 can extend over the top 34 and the flange 40 of the flexible sleeve 32 and can be adhered to a portion of the top 14 of the housing 12. A portion of the cover 42 can also extend over and/or can be adhered to a top surface of the tab 22 of the housing 12.

The protective cover 42 can be provided to protect components and portions of the cap 10, such as the housing 12, flexible sleeve 32, seal 64, and absorbent member 62, during transport and storage to prevent contamination and to prevent the cleaning or disinfecting solution from evaporating prior to use. The protective cover 42 can comprise a sheet, such as a polymer film, with adhesive on a first side of the sheet for removably mounting the protective cover 42 to the open top of the housing 12. Alternatively, the protective cover 42 can be removably mounted to the open top 14 of the housing 12 by heat sealing. The protective cover 42 can be formed from a material that is impervious or substantially impervious to air, so that the cleaning or disinfecting solution on the absorbent member 62 does not evaporate or dry-out. Accordingly, the protective cover 42 can increase a shelf life of the cap 10, as well as prevent microbes and other debris from collecting in the cap 10 prior to use.

Method for Attaching a Connector to the Cap

Figure 6A:
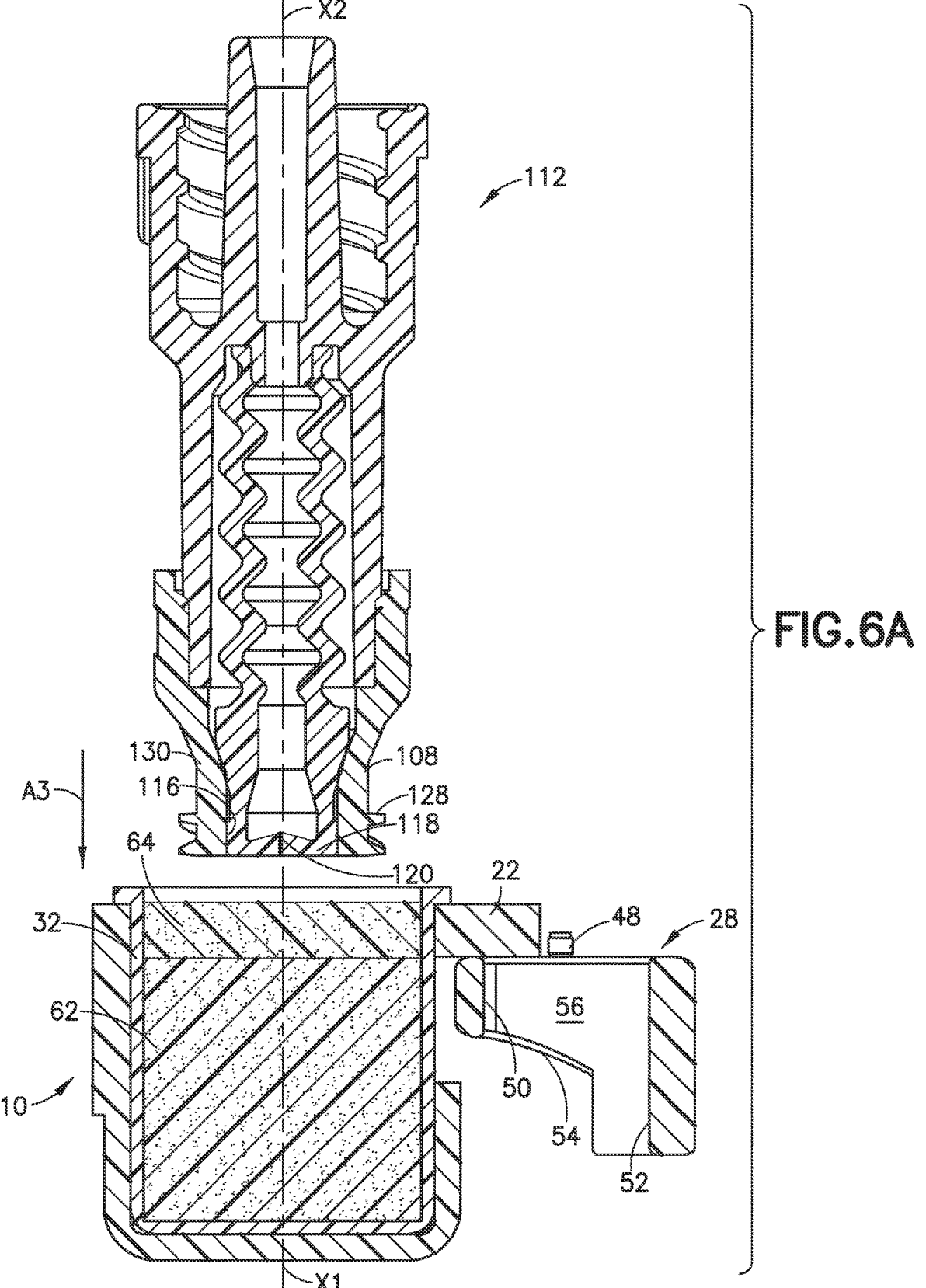
FIG. 6A is a cross sectional view of the cap of FIG. 2A and a female connector, prior to inserting the female connector into the cap.
Figure 6B:
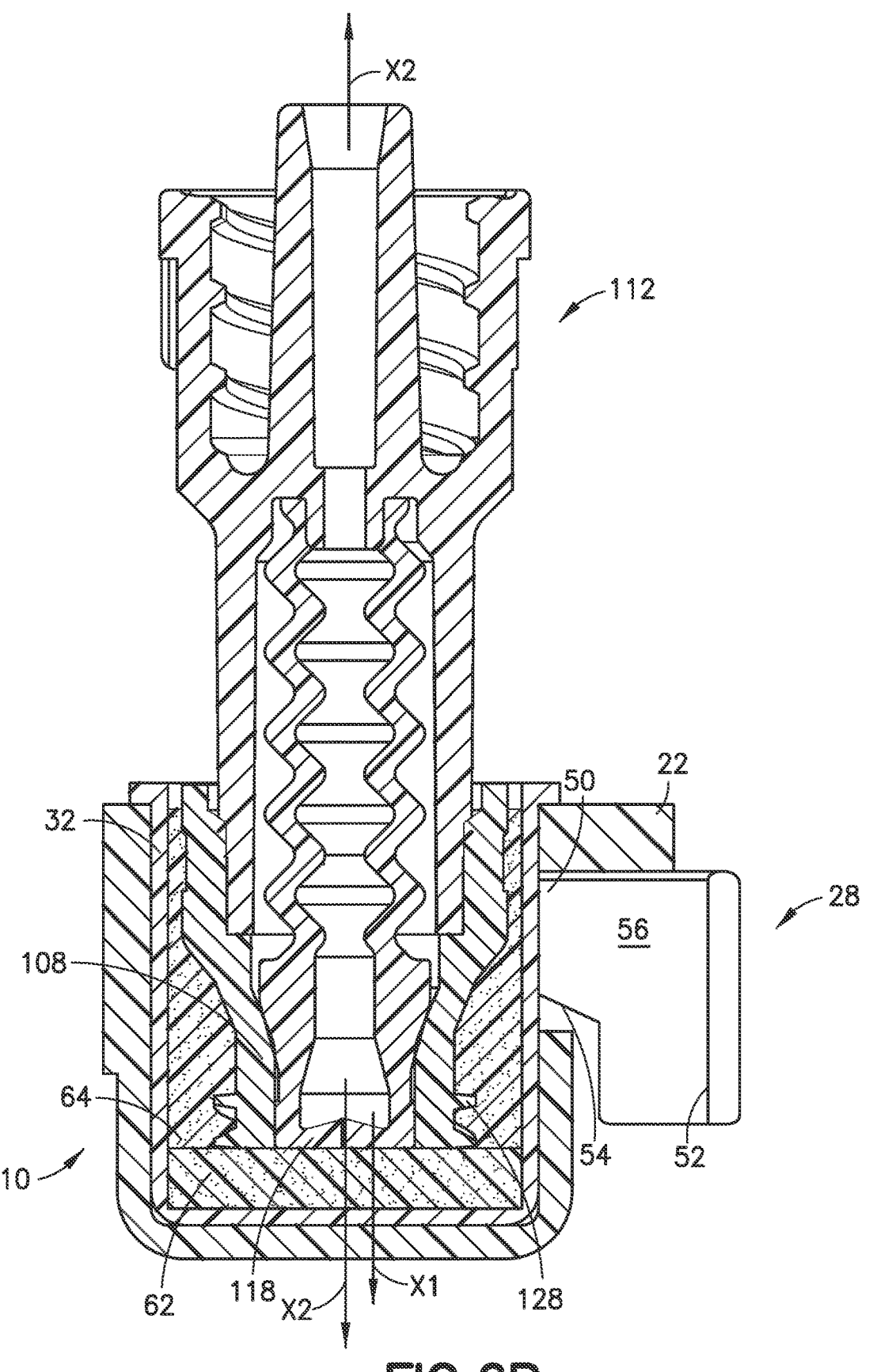
FIG. 6B is a cross sectional view of the cap of FIG. 2A with the female connector inserted into the cap.
Figure 6C:
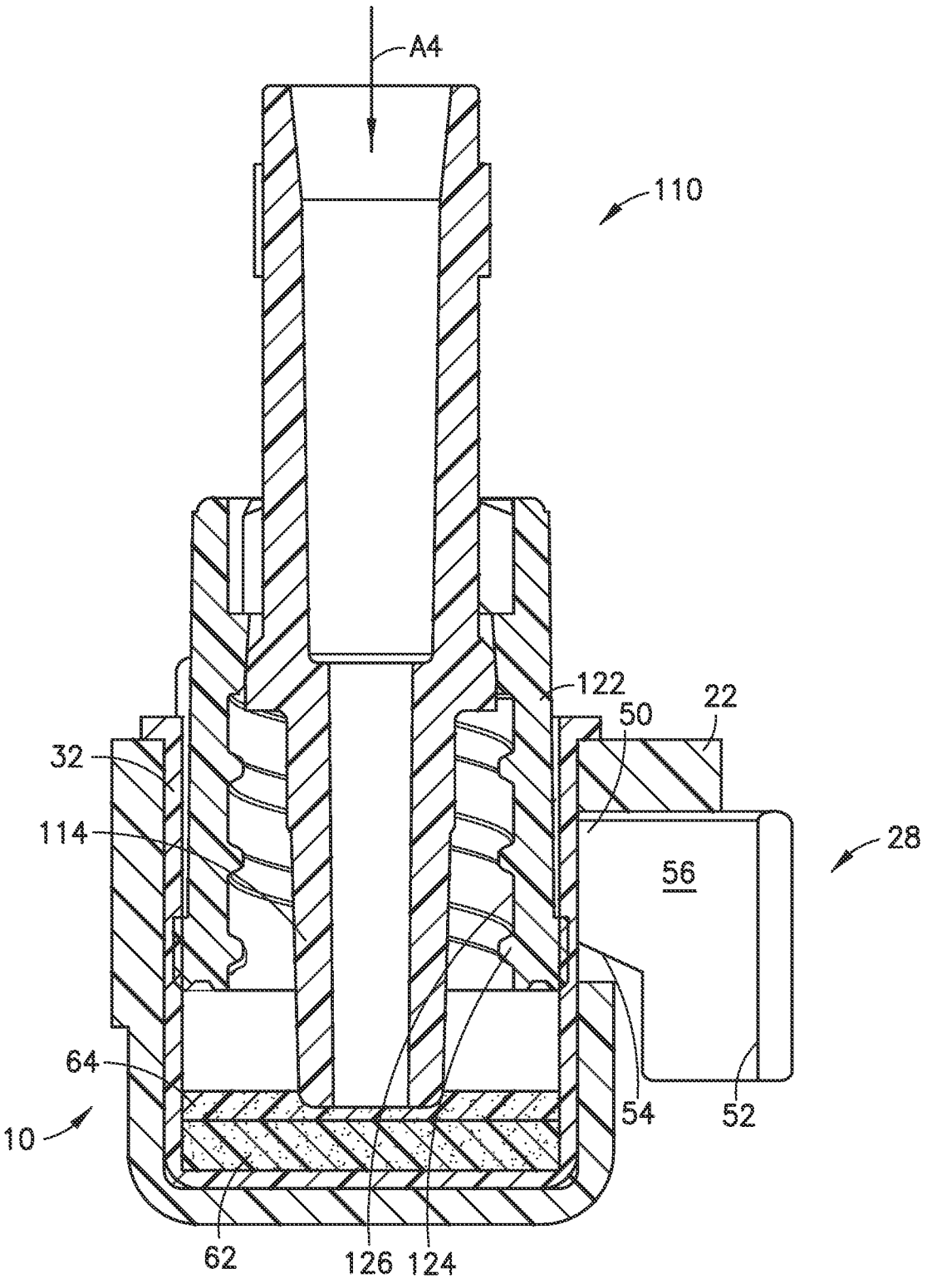
FIG. 6C is a cross sectional view of the cap of FIG. 2A with a male connector inserted into the cap.
Figure 7:
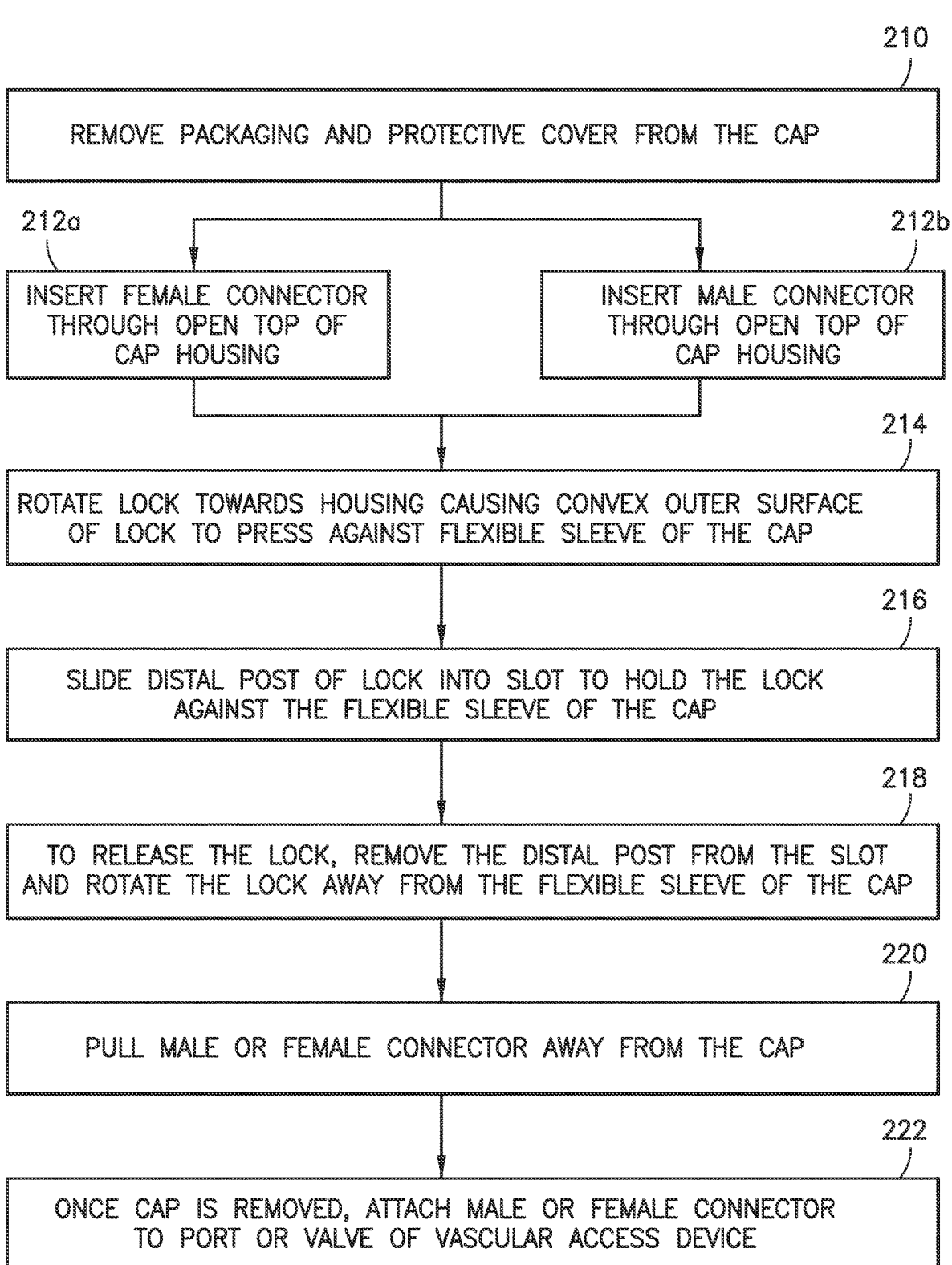
FIG. 7 is a flow chart showing a method for attaching a universal cap to a male connector and a female connector.

As previously described, the cap 10 of the present disclosure is a universal cap 10 configured to be connected to various types and sizes of male connector 110 and female connectors 112. For example, FIGS. 6A and 6B show the cap 10 being connected to a female connector 112. FIG. 6C shows the cap 10 connected to a male connector 110. FIG. 7 is a flow chart showing a method for connecting and/or disconnecting the universal cap 10 from a male connector 110 and a female connector 112.

As shown in FIG. 7, as step 210, in order to connect the cap 10 to a male connector 110 or a female connector 112, the practitioner first removes any packaging from the cap 10 and removes the protective cover 42 from the open top 14 of the housing 12.

At steps 212a, 212b, once the packaging and protective cover 42 are removed, the practitioner moves the connector 110, 112, towards the open top 14 of the housing 12. For example, for a female connector 112 (shown at step 212a), the practitioner moves the female connector 112 toward the housing 12, as shown by arrow A3 in FIG. 6A, causing the septum 118 of the female connector 112 to contact the seal 64 of the cap 10. Continuing to move the female connector 112 into the housing 112 can bring outer surfaces 130 and threads 128 of the tubular distal portion 108 of the female connector 112 into contact with the seal 64. As previously described, contact between abrasive surfaces of the seal 64 and surfaces of the female connector 112 can mechanically remove particles, such as microbes and other debris, from surfaces of the female connector 112, which contributes to the cleaning effect provided by the cap 10.

For the male connector 110, as shown at step 212b, the practitioner moves the male connector 110 in a direction of arrow A4 (shown in FIG. 6C) towards the open top 14 of the housing 12, causing the stem 114 of the male connector 110 to be partially inserted into the housing 12 and bringing the distal tip of the stem 114 into contact with the seal 64. Continuing to move the male connector 110 into the housing 12 also brings a distal end of the annular shield 122 into contact with the seal 64. As previously described, the contact between surfaces of the male connector 110 and the seal 64 can mechanically remove particles, such as microbes and other debris, from the male connector 110.

Continuing to apply axial pressure to the connector 110, 112 causes distal portions of the connector 110, 112 to insert farther into the housing 12 and flexible sleeve 32, thereby axially compressing the absorbent member 62. Compression of the absorbent member 62 releases the cleaning or disinfecting solution, causing the cleaning or disinfecting solution to contact portions of the connector 110, 112. In particular, cleaning solution can contact and disinfect surfaces of the stem 114 and annular shield 122 of the male connector 110. When a female connector 112 is inserted into the cap 10, the cleaning solution can contact and disinfect portions of the female connector 112 including the septum 118, as well as outer surfaces 130 and threads 128 of the tubular distal portion 108 of the female connector 112.

Once the distal portion of the connector 110, 112 is seated in the flexible sleeve 32 of the cap 10 by a sufficient amount, the practitioner can use the lock 28 to secure the cap 10 to the connector 110, 112. For example, as shown in FIG. 6C, the male connector 110 can be inserted into the housing 12 such that a distal end of the annular shield 122 is positioned beyond the opening 20 in the sidewall 18 of the housing 12. Accordingly, when the lock 28 is closed, the flexible sleeve 32 contacts a sidewall of the shield 122 as shown in FIG. 6C. As shown in FIG. 6B, the female connector 112 can be inserted into the housing 23 far enough that the tubular distal portion 108 of the female connector 112 is positioned past the opening 20 of the sidewall 18 of the housing 12. Accordingly, when the lock 28 is closed, the flexible sleeve 32 is pressed against a widest portion of the female connector 112, as shown in FIG. 6B.

More specifically, in order to engage the lock 28, at step 214, the practitioner first presses the lock 28 in a first direction (shown by arrow A1 in FIGS. 4A and 4B) to move the convex outer surface 58 of the cam portion 54 through the opening 20 of the sidewall 18 towards the flexible sleeve 32. The outer convex surface 58 contacts the flexible sleeve 32 deforming the sleeve 32 radially inward, which causes the flexible sleeve 32 to press against the connector 110, 112.

The practitioner continues to apply the pressure the lock 28 until the lock 28 is tight enough to secure the connector 110, 112 in the cap 10.

At step 216, once the lock 28 is sufficiently tight, the practitioner can slide the lock 28 in an upwards direction to insert the distal post 48 of the lock 28 into the slot 26 of the tab 22 of the housing 12. As previously described, inserting the distal post 48 into the slot 26 secures the lock 28 in the closed position preventing the lock 28 from loosening until the distal post 48 is removed from the slot 26.

At step 218, in order to remove the cap 10 from the connector 110, 112, the practitioner first releases the lock 28 by removing the distal post 48 from the slot 26 and rotating the lock 28 away from the flexible sleeve 32 in a second direction (shown by arrow A2 in FIGS. 5A and 5B).

At step 220, once the lock 28 is released, the practitioner grasps the housing 12 of the cap 10 with one hand and the connector 110, 112 with the other hand. The practitioner then pulls the connector 110, 112 away from the cap 10 to remove the connector 110, 112 from the cap 10. As previously described, the inner surface of the flexible sleeve 32 does not include threads. Therefore, the practitioner does not need to twist or rotate the connector 110, 112 relative to the cap 10 to remove the connector 110, 112 from the cap 10. Instead, once the lock 28 is released, the practitioner need only pull the connector 110, 112 axially away from the cap 10 to remove the cap 10. Once removed, the cap 10 can be discarded, as it is often a single use product.

Once the connector 110, 112 is fully removed from the housing 12, at step 222, the connector 110, 112 can be connected to a VAD. For example, the connector 110, 112 can be attached or inserted into a hub, port, or valve of the VAD forming a needleless fluid-tight connection between the connector 110, 112 and a fluid path, channel, or lumen of the VAD.

While examples of the universal cap 10 and methods of use of the present disclosure are shown in the accompanying figures and described hereinabove in detail, other examples will be apparent to, and readily made by, those skilled in the art without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A cap configured to engage at least a first connector and a second connector of different types, the cap comprising:
   a housing comprising an open first end, a second end, at least one sidewall extending between the open first end and the second end, and at least one opening extending through the at least one sidewall;
   a flexible sleeve disposed in the housing comprising a first end, a second end, and a sleeve sidewall extending between the first end of the flexible sleeve and the second end of the flexible sleeve;
   a lock connected to the housing configured to move through the at least one opening through the at least one sidewall of the housing to press against the sleeve sidewall, which causes the sleeve sidewall to directly or indirectly
   press against a portion of the first connector or the second connector to secure the first connector or the second connector in the housing; and
   an absorbent member disposed in the flexible sleeve configured to contain a cleaning solution for cleaning and/or disinfecting portions of the first connector or the second connector engaged to the cap.

2. The cap of claim 1, wherein the first connector is a female connector and the second connector is a male connector.

3. The cap of claim 1, wherein an inner surface of the flexible sleeve is a cylindrical surface without threads or grooves.

4. The cap of claim 1, wherein a removable connection between the lock and the housing holds the lock against the flexible sleeve, thereby securing the first connector or the second connector in the housing.

5. The cap of claim 1, wherein the flexible sleeve comprises a thermoplastic elastomer comprising at least one of silicone, polypropylene, polyethylene, or synthetic or natural rubber (e.g., isoprene).

6. The cap of claim 1, wherein the first end of the flexible sleeve comprises an opening and a flange extending about the opening of the first end of the flexible sleeve, and wherein the flange rests against the open first end of the housing.

7. The cap of claim 1, wherein the lock is configured to cause the flexible sleeve to deform radially inward to directly or indirectly contact the portion of the first connector or the second connector that the sleeve is configured to press against.

8. The cap of claim 1, wherein the housing further comprises a tab extending from the at least one sidewall of the housing, and wherein the lock is rotatably engaged to the tab, such that the lock is configured to rotate relative to the tab to press against the flexible sleeve.

9. The cap of claim 8, wherein the tab of the housing further comprises a slot and wherein a portion of the lock is configured to insert into the slot to hold the lock in contact with the flexible sleeve.

10. The cap of claim 9, wherein the lock comprises a proximal end that is connected to the tab of the housing, a distal end opposite the proximal end, and a cam portion between the proximal end and the distal end of the lock.

11. The cap of claim 10, wherein the cam portion comprises a concave inner surface and a convex outer surface, and wherein rotation of the lock relative to the housing is configured to cause the convex outer surface of the cam portion to contact the flexible sleeve.

12. The cap of claim 10, wherein the distal end of the lock comprises a handle configured to be grasped by a user to rotate the lock towards the flexible sleeve.

13. The cap of claim 10, wherein the proximal end of the lock comprises a proximal post configured to be inserted in a hole in the tab of the housing thereby forming a rotation point for rotation of the lock relative to the housing, and the distal end of the lock comprises a distal post configured to be inserted into the slot of the tab of the housing for holding the lock in a position pressing against the flexible sleeve.

14. The cap of claim 13, wherein the slot comprises a plurality of protrusions configured to engage the distal post to hold the lock in position relative to the flexible sleeve.

15. The cap of claim 1, wherein a pressing force of the lock against the flexible sleeve is configured to cause the first connector or the second connector to be retained within the flexible sleeve in a position where a longitudinal axis of the first connector or the second connector is offset from a longitudinal axis of the housing of the cap.

16. The cap of claim 1, further comprising a seal disposed in the housing over the absorbent member to clean and disinfect the first connecter or the second connector as the first connector or the second connector is inserted into the housing.

17. The cap of claim 1, wherein the absorbent member comprises an open cell foam comprising a thermoplastic elastomer, the cap further comprising the cleaning solution absorbed by the absorbent member, wherein the cleaning solution comprises Isopropyl Alcohol (IPA).

18. The cap of claim 1, further comprising a protective cover over the open first end of the housing.

19. A method for attaching the cap of claim 1 to the first connector or the second connector, the method comprising:

inserting a distal end of the first connector or the second connector through the open first end of the housing and the first end of the flexible sleeve;

applying axial pressure to the first connector or the second connector causing the absorbent member to axially compress and moving the distal end of the first connector or the second connector farther into the flexible sleeve; and moving a portion of the lock through the at least one opening of the at least one sidewall of the housing, thereby pressing the flexible sleeve directly or indirectly against the first connector or the second connector to retain the first connector or the second connector within the housing.

20. A cap comprising:

a housing comprising an open first end, a second end, at least one sidewall extending between the open first end and the second end, at least one opening extending through the at least one sidewall, and a tab extending outward from the at least one sidewall of the housing, the tab comprising a hole and a slot;

a flexible sleeve disposed in the housing comprising a first end, a second end, and a sleeve sidewall extending between the second end of the flexible sleeve and the first end of the flexible sleeve;

a lock comprising (i) a proximal post inserted into the hole of the tab providing a rotation engagement between the lock and the tab, and (ii) a distal post configured to insert into the slot of the tab to prevent rotation of the lock relative to the tab; and an absorbent member disposed in the flexible sleeve configured to contain a cleaning solution for cleaning and/or disinfecting portions of the first connector or the second connector engaged to the cap.

* * * * *